United States Patent [19]

Stoss et al.

[11] Patent Number: 4,891,373
[45] Date of Patent: Jan. 2, 1990

[54] AMINOPROPANOL DERIVATIVES OF 1,4:3,6-DIANHYDROHEXITOL NITRATES, PROCESSES FOR THEIR PREPARATION AND THEIR USE AS MEDICAMENTS

[75] Inventors: Peter Stoss, Illertissen; Matyas Leitold, Biberach; Rodney Yeates, Tiefenbach, all of Fed. Rep. of Germany

[73] Assignee: Pfizer Inc., New York, N.Y.

[21] Appl. No.: 275,315

[22] Filed: Nov. 23, 1988

[51] Int. Cl.⁴ ............... A61K 31/34; A61K 31/455; C07D 493/04
[52] U.S. Cl. ............... 514/228.2; 514/233.8; 514/253; 514/321; 514/422; 514/452; 514/470; 544/153; 544/377; 544/295; 544/360; 546/197
[58] Field of Search ............... 514/228.2, 233.8, 253, 514/321, 422, 452, 470; 544/153, 377, 295, 360; 546/197

[56] References Cited

U.S. PATENT DOCUMENTS 4,363,805 12/1982 Klessing ............... 514/166

FOREIGN PATENT DOCUMENTS 0044940 5/1982 European Pat. Off.
0167008 1/1986 European Pat. Off.

OTHER PUBLICATIONS

M. Leitold et al., Drug Res., 36,1454 (1986)
I. Lepran et al., L. Szekeros, "A Method of Acute Coronary Occlusion in Anesthetized Closed Chest Rats", Acta Physiologica Sci. Hungaricae 53,190 (1979).
B. G. Main and H. Tucker, Recent Advances in β-Adrenergic Blocking Agents, Progress in Medicinal Chemistry 22, G. P. Ellis and G. B. West Editors, Elsevier, 1985, pp. 121 et seq.

Primary Examiner—Mukund J. Shah
Assistant Examiner—C. L. Cseh
Attorney, Agent, or Firm—Peter C. Richardson; Paul H. Ginsberg; Karen DeBenedictis

[57] ABSTRACT

Novel aminopropanol derivatives of 1,4:3,6-dianhydrohexitol nitrates of the general formula I

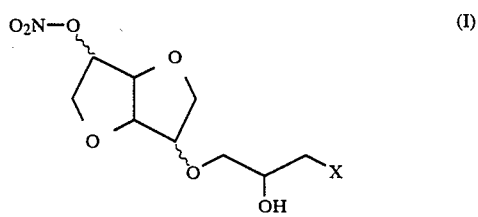

in which X has the meaning given in the specification, processes for their preparation and their use in preventing and treating angina pectoris, systemic hypertension and pulmonary hypertension in mammals.

21 Claims, No Drawings

AMINOPROPANOL DERIVATIVES OF 1,4:3,6-DIANHYDROHEXITOL NITRATES, PROCESSES FOR THEIR PREPARATION AND THEIR USE AS MEDICAMENTS

The present invention relates to aminopropanol derivatives of 1,4:3,6-dianhydro-hexitol nitrates. The compounds are useful in the treatment of angina pectoris, systemic hypertension and pulmonary hypertension in mammals.

1,4:3,6-Dianhydro-hexitol derivatives which contain a substituted 3-amino-2-propanol side chain were described for the first time in European Patent Publication No. 167,008. It is known that this functional group is the typical structural feature of a class of so-called β-receptor blockers. All the representatives of this type of active compound currently used in therapy contain either an isopropylamino group or a tert.-butylamino group as the basic radical. From the findings available to date, these two amino groups appear to represent the optimum of synthetic efforts in the field of β-antagonistic actions. See, for example, B. G. Main and H. Tucker, Recent Advances in β-Adrenergic Blocking Agents, in "Progress in Medicinal Chemistry 22", G. P. Ellis and G. B. West Editors, Elsevier, 1985, page 121 et seq.

The compounds described in European Pat. No. 167,008 contain, as the amine component, straight-chain or branched alkyl- and dialkylamines or those in which the amine nitrogen is the constituent of a purine ring system. When these known amine radicals are replaced by those disclosed in the present application, the resulting compounds are not only more effective β-receptor blockers, they also have unexpected activity as vasodilators.

The present invention relates to novel aminopropanol derivatives of 1,4:3,6-dianhydrohexitol nitrates of the formula I.

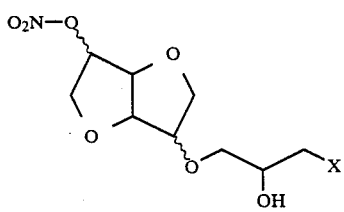

in which X is a benzo[1,4]dioxinyl-2-methylamine radical of the formula

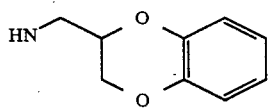

a phenoxyethylamino radical of the formula

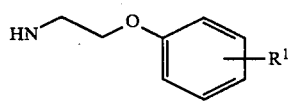

in which $R^1$ is hydrogen, hydroxyl or a $C_1$–$C_3$ alkoxy radical (e.g., a methoxy or ethoxy radical), and the substituent $R^1$ can be in the o-, m- or p-position, or X is one of the following radicals:

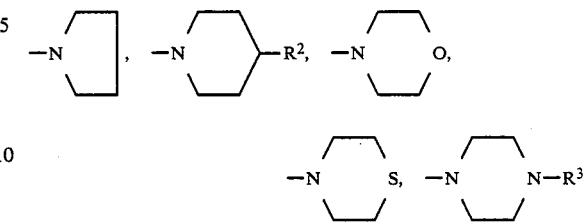

in which $R^2$ represents hydrogen or an unsubstituted or mono-, di- or tri- substituted phenyl radical, wherein the substituents on the phenyl can be the same or different and are selected from $C_1$–$C_3$ alkyl, $C_1$–$C_3$ alkoxy, halogen (i.e. F, Cl, Br or I), nitro and trifluoromethyl, and in which $R^3$ represents straight chain or branched $C_1$–$C_6$ alkyl, (e.g., methyl, ethyl, propyl, isopropyl, butyl, pentyl or hexyl) hydrogen,

wherein $R^6$ is $C_1$–$C_7$ alkyl, phenyl, phenyl substituted with $C_1$–$C_4$ alkyl, or

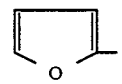

(e.g., acetyl, propionyl, butanoyl, octanoyl, benzoyl, toluyl or furoyl), benzyl, benzhydryl, pyridyl, pyrimidinyl, or unsubstituted or substituted phenyl of the formula

in which $R^4$ and $R^5$ can be identical or different and each represents hydrogen, hydroxyl, $C_1$–$C_6$ alkyl (e.g. methyl, ethyl, propyl or butyl), $C_1$–$C_6$ alkoxy (e.g. methoxy, ethoxy, propoxy, isopropoxy or butoxy), halogen (i.e. F, Cl, Br or I), nitro or trifluoromethyl, or in which $R^4$ and $R^5$ together form a methylenedioxy group, and pharmaceutically acceptable salts thereof.

The present invention also relates to a process for preparing a compound of the formula I comprising reacting a compound of the formula IV, described below, with HX, wherein X is as defined above, or reacting a compound of the formula VIII, described below, with nitric acid. The present invention also relates to a method for preparing a compound of the formula VIII comprising reacting a compound of the formula VII, described below, with a compound of the formula HX wherein X is as defined above.

The compounds of the formula I may be considered derivatives of 1,4:3,6-dianhydro-hexitol, which is also called isohexide. The latter compound can occur in stereoisomeric forms. The invention thus relates to 1,4:3,6-dianhydro-D-mannitol (isomannide) derivatives of the following structure (Ia)

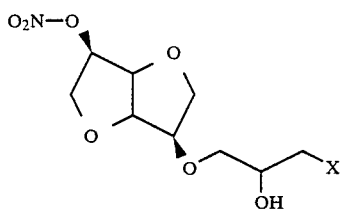

in which the two substituents in the 2- and 5-position are in the endo-position and X is a defined above, and salts thereof; 1,4:3,6-dianhydro-L-iditol (isoidide) derivatives of the following structure (Ib)

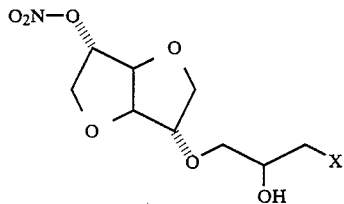

in which the two substituents in the 2- and 5-position are in the exo-position and X is defined above, and salts thereof; and 1,4:3,6-dianhydro-D-glucitol (1,4:3,6-dianhydro-D-sorbitol, isosorbide) derivatives of the following structure (Ic, Id)

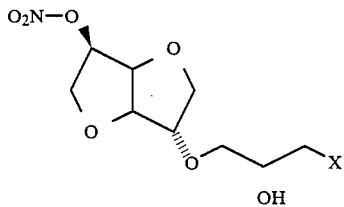

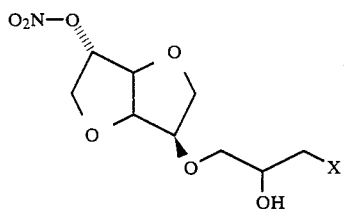

in which X is as defined above, and salts thereof. In naming compounds of the structures Ic and Id, it should be understood, as commonly agreed, that the substituent in the 2-position each time occupies the exo-position and the substituent in the 5-position each time occupies the endo-position.

1,4:3,6-Dianhydro-hexitols have four chiral centers, that is to say carbon atoms 2, 3, 4 and 5. They are therefore optically active compounds. The starting substances used to prepare the compounds according to the invention are present in the optically pure form, as the D-isomannide, L-isoidide and D-isosorbide. The 3-amino-2-propanol side chain

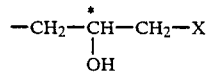

contained in the compounds of the formula I likewise has a center of asymmetry in carbon atom 2, which gives rise to the existence of R- and S-configurated enantiomeric forms of this side chain. For this reason, the compounds of the formula I occur as diastereoisomers. The present invention relates both to the diastereoisomer mixtures and to the separate components of uniform configuration.

The compounds of the formula I can be prepared by various routes using known synthetic methods. Some of these routes are described below.

The compounds of the formula I can be obtained, for example, by converting isohexide nitrate of the formula II into an O-(2,3-epoxypropyl)-isohexide nitrate of the formula IV either directly, by reaction with a 2,3-epoxy-1-halogeno-propane, or indirectly, by reaction with an allyl halide, via the intermediate stage III and with subsequent oxidation, and converting this product into the desired product I by reaction with HX, in which X is as defined above.

The reaction of the compound of the formula IV with HX is conducted either in a suitable inert solvent or without any solvent. Suitable solvents include polar protic solvents, such as lower alcohols, open chain or cyclic ethers or aprotic solvents. Preferred solvents are methanol, ethanol, 1-propanol, 2-propanol, 1-butanol, tetrahydrofuran, dioxane, dimethoxyethane, diethoxyethane, acetonitrile, DMF and DMSO. Methanol, ethanol, 1-propanol and 2-propanol are especially preferred. The reaction takes place at a temperature between about 0° and about 150° C., preferably between room temperature and the reflux temperature of the appropriate reaction mixture. The time for completion of the reaction is, of course, dependent on the temperature applied and can vary from 1 hour to 48 hours. In particular, when conducted at room temperature, the reaction is run for about 20 to about 30 hours and when conducted at reflux temperature for about 1 to 6 hours. The ratio of compound IV to HX may include a stoichiometric ratio as well as an excess of each of the components of between about 1.5:1 and about 1:5. Preferably a nearly stoichiometric ratio is used.

The compounds of the formula I may also be prepared by converting an isohexide of the formula V into an O-(2,3-epoxypropyl)-isohexide of the formula VII, it being possible for this reaction to be carried out either directly, by means of a 2,3-epoxy-1-halogeno-propane, or in 2 stages, by initial reaction of V with an allyl halide to form the allyl ether VI and subsequent oxidation to VII. Compound VII is then reacted with HX, in which X is as defined above, to form an O-(3-amino-2-hydroxypropyl)-isohexide VIII, and this is converted into the desired compound I by esterification with nitric acid.

Finally, another systhesis route leads via the O-allyl-isohexides VI, which can be obtained as described above, by esterifying VI with nitric acid to give the O-allyl-isohexide nitrates III and then converting these into the end products I as described above.

The nitrate ester formation, which comprises the steps from VI to III and from VIII to I in the reaction scheme, can be conducted by reacting a compound VI or VIII respectively with a nitrate ester forming reagent, such as fuming nitric acid or a mixture of fuming nitric acid and concentrated sulfuric acid, or a mixture of 65 percent nitric acid and acetic anhydride, under low temperature in the presence or absence of an inert solvent. The reaction temperatures are generally in the range between −60° C. and room temperature, preferably between about 0° C. and −20° C. The molar ratio of reactants is in the range of about 1 to about 10.

Preparation process

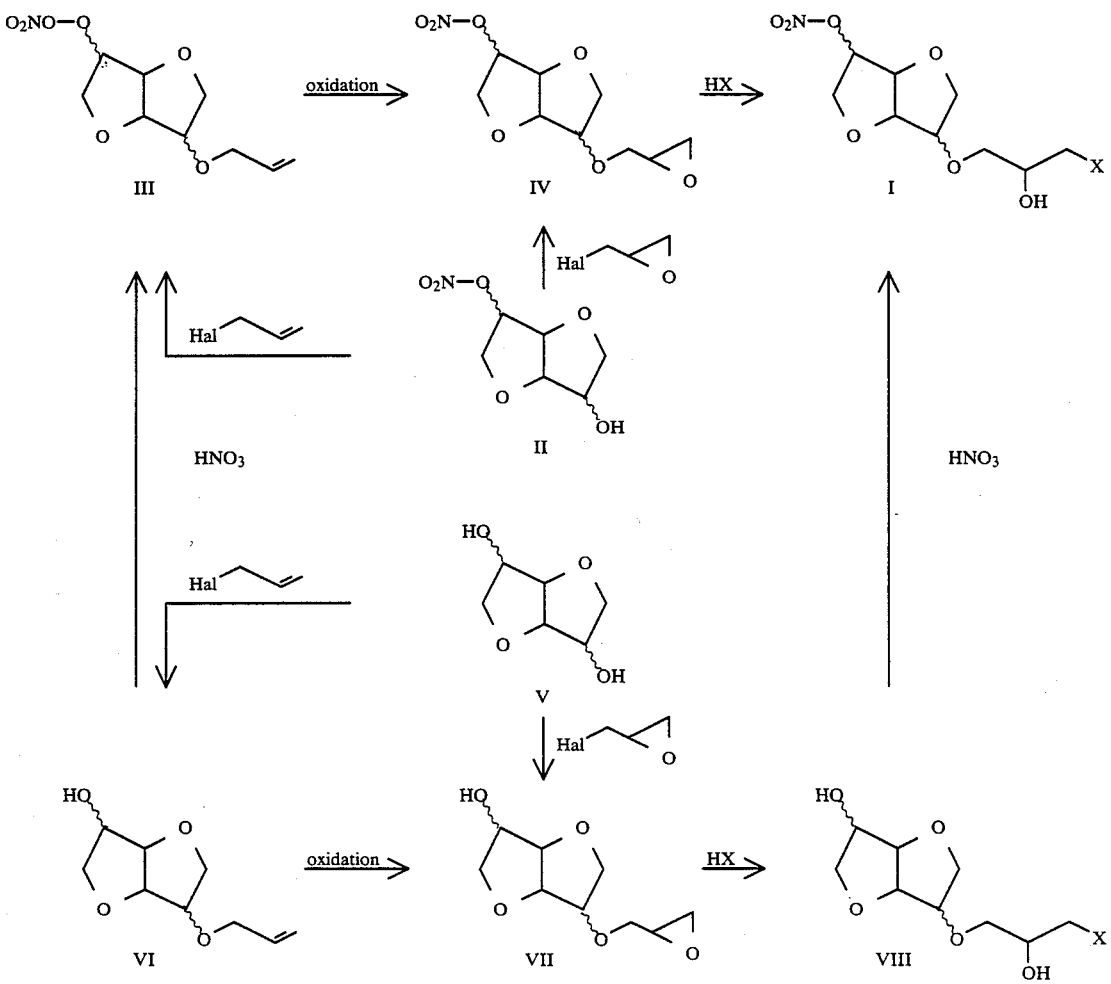

If the compounds II or V are allowed to react with racemic halogenoepoxypropanes, diastereoisomer pairs of IV and VII result. The same is true if the corresponding allyl ethers III or VI are epoxidized. On the other hand, if enantiomerically pure epoxides are reacted with II or V, in each case only a uniform diastereoisomeric product IV or VII is obtained. All other subsequent reactions, of IV to I or of VII via VIII to I, accordingly can also be carried out either with the diastereoisomer mixtures or with uniform diastereoisomers. Where diastereoisomer mixtures are present, it is also possible for separation into the two optically uniform components to be carried out either at any of the intermediate stages IV, VII and VIII or at the stage of the final products of the formula I. The customary separation techniques, such as, for example, crystallization, distillation, chromatographic processes and the like, can be used here.

When the reaction has ended, the reaction products of the formula I are isolated and purified in the customary manner and if appropriate converted into the salt of an inorganic or organic acid, preferably into a pharmaceutically acceptable salt. Examples of such salts are hydrochlorides, hydrobromides, nitrates, sulfates, phosphates, acetates, oxalates, maleates, fumarates, tartrates, lactates, maleates, malonates, citrates, salicylates, methanesulfonates, benzenesulfonates, toluenesulfonates and naphthalenesulfonates.

These or other salts of the new compound, such as, for example, picrates, can also be used to purify the free bases obtained, by converting the free base into a salt, separating the salt and if appropriate recrystallizing it or purifying it by another means, and liberating the base again from the salt.

The compounds of the formula II and V used as starting substances have been known for a long time. The intermediate products III, IV, VI and VII have already been mentioned in European Pat. No. 167,008. The compounds of the formula VIII are novel compounds.

Surprisingly, the compounds of the formula I and the pharmaceutically acceptable salts thereof are distinguished by a broad pharmacological action spectrum. In particular, they have a pronounced cardiovascular action. On isolated strips of veins from dogs, they act against the K+-induced contraction in a lower concentration than on aorta strips. On isolated hearts from guinea pigs, they increase coronary flow as a function of the dose. On anesthetized rats, they prevent lypressin coronary spasm as a function of the dose and significiantly increase the survival rate of rats following acute cardiac infarction. On normotensive conscious dogs, they lower the systolic blood pressure for a period of 6-8 hours after oral administration. On artifically respirated anesthetized, thoraxotomized dogs, they reduce the mean arterial pressure, the left ventricular systolic pressure, the left ventricular end diastolic pressure and the pressure in the Arteria pulmonalis and reduce the peripheral vascular resistance. In contrast to the known organic nitrate esters, they also lead to a long-lasting reduction in the systolic blood pressure of spontaneously hypertensive rats. Such an action profile is not known for any of the substances of similar structure which have already been described.

Set forth below is data obtained on the compounds of Examples 17, 19 and 20 that illustrates the pharmacological action of the compounds of the present invention. Mice tolerated 500 mg/kg perorally of the compound of Examples 17, 19 and 20 without clinical symptoms and without fatal consequences.

TABLE 1

Influence of various compounds on the T-wave increase in the ECG of the anesthetized rat induced by intravenous bolus injection of lypressin was determined following the method of M. Leitold et al., Drug Res., 36, 1454 (1986). The substances were administered perorally 30 minutes or at various times before the lypressin injection.

| Substance | n | Dose mg/kg | $ED_{50}$ value | 95% confidence limits | Duration of action at the $ED_{50}$ dose in hours |
|---|---|---|---|---|---|
| Example 17 | 30 | 50-100 | 89.52 | 78.33-102.30 | 2 |
| Example 20 | 18 | 50-100 | 73.82 | 65.89-82.69 | 4 |
| Example 19 | 18 | 12.5-50.0 | 46.72 | 22.87-58.96 | 4 |

TABLE 2

Influence of various substances on the survival rate of rats 60 minutes, 24 hours and 7 days after an acute coronary ligature was determined following the method of I. Lepran, et al., L. Szekeres, Acta Physiologica Sci. Hungaricae 53, 190 (1979). The substances were administered orally 5 minutes before the acute coronary ligature.

| Substance | n | Dose mg/kg | Number of rats surviving after an acute coronary ligature | | |
|---|---|---|---|---|---|
| | | | 60 minutes | 24 hours | 7 days |
| Control | 80 | 0.5 ml 1% CMC | 23/80 | 21/80 | 21/80 |
| Example 17 | 20 | 30.0 | 17/20** | 17/20** | 17/20** |
| Example 20 | 20 | 100.0 | 14/20* | 14/20* | 14/20* |
| Example 19 | 20 | 100.0 | 15/20* | 15/20* | 15/20* |

Significant difference from the control
*p 0.05
**p 0.01

TABLE 3

Cardiovascular actions of Example 17 following intravenous administration to anesthetized dogs (pentobarbital) with an opened thorax and artificial respiration.

| n | Dose µg/kg | Parameter | | Pre-value | Action of substance | Change | Duration of action (minutes) |
|---|---|---|---|---|---|---|---|
| 4 | 30.0 | MAP | (mmHg) | 105 ± 2 | 83 ± 1 | 23 ± 2*** | 14 ± 1 |
| | | HR | (Bts/M) | 198 ± 17 | 219 ± 18 | 21 ± 18 | 6 ± 2 |
| | | LVSP | (mmHg) | 150 ± 4 | 131 ± 9 | 19 ± 6* | 5 ± 3 |
| | | LVEDP | (mmHg) | 6.3 ± 0.7 | 6.2 ± 0.7 | 0.2 ± 0.03* | 2.2 ± 1.3 |
| | | $dp/dt_{max}$ | (mmHg/s) | 3568 ± 259 | 3144 ± 166 | 424 ± 95 | 8 ± 3 |
| | | TPR | (mmHg/ml) | 88 ± 15 | 65 ± 12 | 23 ± 4* | >14 |
| | | PAP | (mmHg) | 18.3 ± 3.4 | 17.0 ± 4 | 1.3 ± 0.5 | 2 ± 0.3 |
| | | SV | (ml/s) | 4.8 ± 3.4 | 52 ± 0.4 | 0.4 ± 0.2 | 2 ± 0.2 |
| | | CO | (l/M) | 0.86 ± 0.06 | 0.93 ± 0.07 | 0.07 ± 0.04* | 6 ± 3 |
| 4 | 300 | MAP | (mmHg) | 104 ± 3 | 49 ± 3 | 55 ± 6*** | 157 ± 39 |
| | | HR | (Bts/M) | 191 ± 20 | 206 ± 15 | 15 ± 13 | 2.4 ± 1 |
| | | LVSP | (mmHg) | 154 ± 4 | 115 ± 4 | 39 ± 5*** | 151 ± 24 |
| | | LVEDP | (mmHg) | 5.7 ± 0.7 | 5.5 ± 0.8 | 0.3 ± 0.1* | 5.6 ± 2 |
| | | $dp/dt_{max}$ | (mmHg/s) | 3680 ± 284 | 2133 ± 310 | 1547 ± 423* | >197 |
| | | TPR | (mmHg/ml) | 84 ± 8 | 42 ± 2 | 42 ± 6 | 163 ± 16 |
| | | PAP | (mmHg) | 19.7 ± 5 | 18.2 ± 5 | 1.5 ± 0.5 | 1.4 ± 0.1 |
| | | SV | (ml/s) | 4.4 ± 0.3 | 3.7 ± 0.4 | 0.7 ± 0.3 | 74 ± 43 |
| | | CO | (l/M) | 0.810 ± 0.099 | 0.684 ± 0.137 | 0.127 ± 0.046 | 73 ± 40 |
| 4 | 3000 | MAP | (mmHg) | 106 ± 2 | 33 ± 2 | 67 ± 4*** | >114 |
| | | HR | (Bts/M) | 163 ± 14 | 182 ± 17 | 20 ± 17 | 1.4 ± 0.3 |
| | | LVSP | (mmHg) | 161 ± 2 | 113 ± 3 | 48 ± 3*** | >74 |
| | | LVEDP | (mmHg) | 6.2 ± 1 | 5.6 ± 1 | 0.6 ± 0.3 | >73 |
| | | $dp/dt_{max}$ | (mmHg/s) | 3847 ± 132 | 2019 ± 123 | 1828 ± 238** | >75 |
| | | TPR | (mmHg/ml) | 118 ± 15 | 44 ± 10 | 74 ± 6*** | 24 ± 6 |
| | | PAP | (mmHg) | 20.4 ± 6 | 18.2 ± 7 | 2.3 ± 0.8* | 2 ± 0.6 |
| | | SV | (ml/s) | 5.6 ± 0.7 | 3.0 ± 0.6 | 2.6 ± 0.4 | >75 |

TABLE 3-continued

Cardiovascular actions of Example 17 following intravenous administration to anesthetized dogs (pentobarbital) with an opened thorax and artificial respiration.

| n | Dose µg/kg | Parameter | | Pre-value | Action of substance | Change | Duration of action (minutes) |
|---|---|---|---|---|---|---|---|
| | | CO | (l/m) | 0.855 ± 0.065 | 0.405 ± 0.055 | 0.450 ± 0.025** | >75 |

Significant difference from the pre-value *p < 0.05, p < 0.01, * p < 0.001
MAP = mean arterial blood pressure
HR = heart rate
LVSP = left ventricular systolic blood pressure
LVEDP = left ventricular enddiastolic pressure
$dp/dt_{max}$ = maximum rate of increase in the left ventricular pressure
TPR = total peripheral vascular resistance
PAP = blood pressure in the A. pulmonalis
SV = stroke volume
CO = cardiac output

TABLE 4

Cardiovascular actions of Example 20 following intravenous administration to anesthetized dogs (pentobarbital) with an opened thorax and artificial respiration.

| n | Dose µg/kg | Parameter | | Pre-value | Action of substance | Change | Duration of action (minutes) |
|---|---|---|---|---|---|---|---|
| 3 | 30 | MAP | (mmHg) | 91 ± 2 | 66 ± 3 | 25 ± 5* | 15 ± 2 |
| | | HR | (Bts/M) | 190 ± 11 | 192 ± 10 | 2 ± 2 | 11 ± 4 |
| | | LVSP | (mmHg) | 138 ± 7 | 116 ± 10 | 22 ± 4* | 8 ± 3 |
| | | LVEDP | (mmHg) | 7.6 ± 1.3 | 7.5 ± 1.2 | 0.1 ± 0.2 | 9 ± 7 |
| | | $dp/dt_{max}$ | (mmHg/s) | 3079 ± 424 | 2321 ± 363 | 758 ± 269 | 15 ± 4 |
| | | TPR | (mmHg/ml) | 65 ± 5 | 63 ± 13 | 2 ± 13 | 4 ± 2 |
| | | PAP | (mmHg) | 16.4 ± 1 | 16.0 ± 1 | 0.4 ± 0.2 | 11 ± 6 |
| | | SV | (ml/s) | 9.8 ± 2 | 7.5 ± 2 | 2.3 ± 1 | 12 ± 6 |
| | | CO | (l/M) | 1.19 ± 0.4 | 0.81 ± 0.3 | 0.38 ± 0.1 | 12 ± 6 |
| 3 | 300 | MAP | (mmHg) | 97 ± 0.7 | 58 ± 2 | 39 ± 3** | 35 ± 15 |
| | | HR | (Bts/M) | 197 ± 14 | 197 ± 12 | | |
| | | LVSP | (mmHg) | 146 ± 6 | 111 ± 11 | 34 ± 5** | 34 ± 12 |
| | | LVEDP | (mmHg) | 7.9 ± 1 | 6.8 ± 1 | 1.1 ± 1 | 18 ± 13 |
| | | $dp/dt_{max}$ | (mmHg/s) | 3109 ± 436 | 2056 ± 385 | 1053 ± 333 | 36 ± 11 |
| | | TPR | (mmHg/ml) | 74 ± 4 | 35 ± 6 | 39 ± 9 | 6 ± 2 |
| | | PAP | (mmHg) | 16.3 ± 1 | 15.7 ± 1 | 0.7 ± 0.3 | 14 ± 13 |
| | | SV | (ml/s) | 6.7 ± 0.4 | 7.2 ± 2.5 | 0.5 ± 2.9 | 33 ± 23 |
| | | CO | (l/M) | 1.11 ± 0.3 | 1.32 ± 0.7 | 0.21 ± 0.6 | 35 ± 23 |
| 3 | 3000 | MAP | (mmHg) | 101 ± 3 | 56 ± 2 | 45 ± 5** | 118 ± 20 |
| | | HR | (Bts/M) | 199 ± 19 | 169 ± 34 | 30 ± 15 | 80 ± 44 |
| | | LVSP | (mmHg) | 153 ± 7 | 98 ± 21 | 55 ± 15** | 128 ± 12 |
| | | LVEDP | (mmHg) | 5.0 ± 2.4 | 2.7 ± 3.8 | 2.3 ± 1.7 | 104 ± 51 |
| | | $dp/dt_{max}$ | (mmHg/s) | 3372 ± 614 | 1977 ± 537 | 1395 ± 263* | >148 |
| | | TPR | (mmHg/ml) | 81 ± 6 | 24 ± 7 | 56 ± 7* | 27 ± 21 |
| | | PAP | (mmHg) | 15.7 ± 1 | 14.6 ± 1 | 1.1 ± 0.3* | >177 |
| | | SV | (ml/s) | 5.6 ± 0.8 | 10.6 ± 3.3 | 50 ± 0.7 | 4 ± 0.0 |
| | | CO | (l/m) | 1.15 ± 0.2 | 2.02 ± 0.8 | 0.87 ± 0.7 | 3 ± 0.4 |

Significant difference from the pre-value *p < 0.05, **p < 0.01
MAP = mean arterial blood pressure
HR = heart rate
LVSP = left ventricular systolic blood pressure
LVEDP = left ventricular enddiastolic pressure
$dp/dt_{max}$ = maximum rate of increase in the left ventricular pressure
TPR = total peripheral vascular resistance
PAP = blood pressure in the A. pulmonalis
SV = stroke volume
CO = cardiac output

TABLE 5

Duration of the action of various substances on the systolic blood pressure (SBP) and heart rate (HR) following peroral administration to conscious beagle dogs.
Mean Values ± SEM

| Substance | n | Dose mg/kg | Parameter | Pre-value | Action of substance after...hours | | | | |
|---|---|---|---|---|---|---|---|---|---|
| | | | | | 1 | 2 | 3 | 6 | 8 |
| Example 17 | 5 | 6.0 | SBP (mmHg) | 123 ± 8 | 91 ± 6** | 89 ± 4** | 97 ± 5** | 101 ± 5** | 115 ± 7 |
| | | | HR (Bts/M) | 85 ± 5 | 101 ± 17 | 110 ± 16 | 89 ± 8 | 89 ± 5 | 85 ± 7 |
| Example 20 | 6 | 5.0 | SBP (mmHg) | 126 ± 4 | 97 ± 8* | 95 ± 6** | 106 ± 4** | 113 ± 4** | 121 ± 3 |
| | | | HR (Bts/M) | 78 ± 6 | 98 ± 7 | 109 ± 10 | 82 ± 7 | 78 ± 6 | 77 ± 6 |
| Example 19 | 6 | 5.0 | SBP (mmHg) | 133 ± 7 | 105 ± 8*** | 105 ± 5*** | 118 ± 6* | 126 ± 6 | NT |
| | | | HR (Bts/M) | 84 ± 5 | 101 ± 5 | 90 ± 5 | 85 ± 5 | 86 ± 5 | NT |

Significant difference in comparison with the control *p < 0.05, p < 0.01, *p < 0.001
NT = not tested The invention therefore also relates to the use of compounds of the formula I and their pharmaceutically acceptable salts in the treatment and prevention of systemic hypertension (also known as high blood pressure), angina pectoris, and pulmonary hypertension in mammals, including humans. A compound of the formula I or a pharmaceutically acceptable salt thereof can be administered alone or in admixture with suitable excipients. Such a mixture may contain one or more compounds of the formula I of pharmaceutically acceptable salts thereof in an amount of 0.1 to 99.9%. A typical dose for an adult human would range from about 1 mg to about 500 mg.

The exact dosage of a compound of the formula I or a pharmaceutically acceptable salt thereof will depend upon such factors as the age, weight and condition of the patient and the severity of disease. In general, however, a therapeutically effective dose of a compound of the formula I or a pharmaceutically acceptable salt thereof will range from about 0.1 to about 20 mg/kg body weight of the subject to be treated per day, preferably about 2 to about 10 mg/kg per day, taken in up to 4 divided doses.

Possible pharmaceutical presentation forms are all the formulations with which the expert if familiar, such as, for example, suppositories, powders, granules, tablets, capsules, suspensions, liquid formulations, injection formulations and transdermal systems. Solid, semi-solid or liquid excipients or diluents can be used to prepare pharmaceutical presentation forms. These agents include correctants, binders, lubricants, emulsifiers and the like. Examples of such agents are: starch, such as potato starch and cereal starch, sugar, such as lactose, sucrose, glucose, mannitol and sorbitol, cellulose, such as crystalline cellulose, methylcellulose, calcium carboxymethylcellulose, sodium carboxymethyl cellulose and hydroxypropylcellulose, inorganic materials, such as potassium phosphate, calcium sulfate, calcium carbonate and talc, gelatin, gum arabic, polyvinylpyrrolidone, surface-active substances, such as fatty acid glycerides, fatty acid sorbitan esters, fatty acid esters of sucrose and polyglycerol, and others.

Some examples of medicament formulations using the compounds according to the invention are given below:

| Tablets: | |
|---|---|
| Composition | mg/tablet |
| compound according to the invention | 3.0 |
| microcrystalline cellulose | 25.0 |
| lactose | 17.0 |
| calcium carboxymethylcellulose | 4.5 |
| magnesium stearate | 0.5 |

The above ingredients are sieved and mixed adequately and thoroughly and the mixture is pressed on a suitable tablet press.

| Capsules: | |
|---|---|
| Composition | mg/capsule |
| compound according to the invention | 10 |
| lactose | 40 |
| microcrystalline cellulose | 30 |
| talc | 10 |

The above ingredients are sieved and mixed adequately and thoroughly, and hard gelatin capsules are filled with the mixture on a suitable capsule filling machine.

The following examples served to illustrate the invention. Unless indicated otherwise, the compounds listed in the examples are in each case diastereoisomer mixtures. The rotation values $[\alpha]_D^{20}$ quoted were measured at a concentration of c=1 in methanol.

The preparation of the isohexide and isohexide nitrate allyl and epoxypropyl ethers used as intermediate products has already been described in European Pat. No. 167,008.

EXAMPLE 1

2-O-(3-Pyrrolidin-1-yl-2-hydroxypropyl)-isosorbide-5-nitrate

A. 2-O-(3-Pyrrolidin-1-yl-2-hydroxypropyl)-isosorbide 10.11 g (0.05 mole) of 2-O-(2,3-epoxypropyl)-isosorbide (EP 167,008) was stirred with 3.56 g (0,05 mole) of pyrrolidine in 100 ml of ethanol for 15 hours at room temperature and then for one hour under reflux. After the solvent had been evaporated off, the residue was taken up in 50 ml of 1 N hydrochloric acid and the mixture was extracted with three 30 ml portions of diethylether. The aqueous phase was subsequently rendered alkaline with dilute sodium hydroxide solution and extracted 3 times with three 100 ml portions of chloroform. The chloroformic solution was dried with sodium sulfate, the chloroform evaporated off and the residue purified by flash chromatography on silica gel using methanol/concentrated ammonia water 99/1 as eluent to obtain the title compound of this step as an oil.

B. The oily product from step A was added dropwise to a mixture of 13 g of 65 percent nitric acid and 45 ml of acetic anhydride at 0–5° C., with stirring. The reaction mixture was allowed to warm slowly to room temperature and was then kept at 50° C. for a further 5 hours. It was subsequently poured into water, made alkaline with sodium carbonate, under cooling, and extracted with methylene chloride. The organic phase was washed with water and concentrated on a rotary evaporator. The reaction product was first purified by flash chromatography on silica gel using methanol/concentrated aqueous ammonia 99/1 as eluent and then converted into the oxalate. $C_{13}H_{22}N_2O_7$; oxalate: m.p. 117°–120° C. (ethanol). $[\alpha]_D^{20} + 83,0$.

EXAMPLE 2

2-O-(3-Piperidino-2-hydroxypropyl)-isosorbide-5-nitrate

A. 2-O-Allyl-isosorbide-5-nitrate 18.62 g (0,1 mole) 2-O-allyl-isosorbide (EP 167,008) was added dropwise to a mixture of 13 g of 65 percent nitric acid and 45 ml of acetic anhydride at 0°–5° C., while stirring. After the mixture had been left at this temperature for a further 15 minutes, it was poured into water and the reaction product extracted with methylene chloride. The organic phase was dried over sodium sulfate and concentrated on a rotary evaporator. The oily product was used in the subsequent stage without further purification.

B. 2-O-(2,3-Epoxypropyl)-isosorbide-5-nitrate 23.1 g (0.1 mole) of the oily material from step A was stirred with 25 g of 3-chloro-perbenzoic acid in 100 ml of chloroform for 24 hours at room temperature. Then the precipitated 3-chloro-benzoic acid was removed by filtration and the filtrate was washed with saturated aqueous sodium sulfate and concentrated on a rotary evaporator. The oily product was used in the following step without further purification.

C. 12.36 g (0.05 mole) of the oily material from step B was stirred with 4.26 g (0.05 mole) of piperidine in 100 ml of ethanol at room temperature for 20 hours. Then the solvent was evaporated, the residue was taken up in 50 ml of 1N hydrochloric acid and the mixture extracted with three 30 ml portions of diethylether. The aqueous phase was subsequently rendered alkaline with dilute sodium hydroxide solution and extracted with three 100 ml portions of chloroform. The residue, which remained after the chloroform solution had been dried over sodium sulfate and concentrated, was purified by flash chromatography on silica gel using methanol as eluent. The oily base was then converted into the citrate. $C_{14}H_{24}N_2O_7$; citrate: m.p. 70°–74° C. (2-propanol), $[\alpha]_D^{20}+63.0$.

EXAMPLE 3

2-O-(3-Morpholino-2-hydroxypropyl)-isosorbide-5-nitrate 12.36 g (0,05 mole) of 2-O-(2,3-epoxypropyl)-isosorbide-5-nitrate was stirred with 4.36 g (0.05 mole) of morpholine in 100 ml of ethanol at room temperature for 20 hours. Then the solvent was evaporated, the residue was taken up in 50 ml of 1N hydrochloric acid and the mixture was extracted with three 30 ml portions of diethylether. The aqueous phase was subsequently rendered alkaline with dilute sodium hydroxide solution and extracted with three 100 ml portions of chloroform. The residue, which remained after the chloroform solution had been dried over sodium sulfate and concentrated, was purified by flash chromatography on silica gel using chloroform/methanol 9/1 as eluent. The oily base was then converted into the hydrochloride. $C_{13}H_{22}N_2O_8$; hydrochloride: m.p. 48° C. (precipitated in diethylether with HCl gas) $[\alpha]_D^{20}+86.0$. The compounds of Examples 4 to 40 were similarly prepared.

EXAMPLE 4

2-O-(3-Thiomorpholino-2-hydroxypropyl)-isosorbide-5-nitrate $C_{13}H_{22}N_2O_7$ S; hydrochloride. 0.25 $H_2O$: melting point 52° C. (precipitated in diethyl ether with HCl gas), $[\alpha]hd D^{20}+82.0$.

EXAMPLE 5

2-O-(3-Piperazinyl-2-hydroxypropyl)-isosorbide-5-nitrate $C_{13}H_{23}N_3O_7$; dihydrochloride . $H_2O$ . 0.5 2-propanol: melting point 71°–76° C. (2-propanol), $[\alpha]_D^{20}+61.0$.

EXAMPLE 6

2-O-[3-(4-Phenyl-piperidino)-2-hydroxpropyl]-isosorbide-5-nitrate $C_{20}H_{28}N_2O_7$; hydrochloride: melting point 129° C. (2-propanol/ether), $[\alpha]_D^{20}+73.5$.

EXAMPLE 7

2-O-[3-(4-Acetyl-piperazinyl)-2-hydroxypropyl]-isosorbide-5-nitrate $C_{15}H_{25}N_3O_8$; hydrochloride. 0.75 $H_2O$: melting point 66° C. (ethanol/ether), $[\alpha]_D^{20}+75.5$.

EXAMPLE 8

2-O-[3-(4-Benzoyl-piperazinyl)-2-hydroxypropyl]-isosorbide-5nitrate $C_{20}H_{27}N_3O_8$; hydrochloride: melting point 169°–172° C. (decomposition) (ethanol) $[\alpha]_D^{20}+65.6$.

EXAMPLE 9

2-O-<3-[4-(2-Furyl-carbonyl)-piperazinyl]-2-hydroxypropyl>-isosorbide-5-nitrate $C_{18}H_{25}N_3O_9$; oxalate . 0.5 $H_2O$: melting point 105°–109° C. (acetonitrile), $[\alpha]_D^{20}+64.0$.

EXAMPLE 10

2-O-[3-(4-Benzyl-piperazinyl)-2-hydroxypropyl]-isosorbide-5-nitrate $C_{20}H_{29}N_3O_7$; dihydrochloride . 0.25 $H_2O$: melting point 182° C. (decomposition) (ethanol), $[\alpha]_D^{20}+62.0$.

EXAMPLE 11

2-O-[3-(4-Benzhydryl-piperazinyl)-2-hydroxypropyl]-isosorbide-5-nitrate $C_{26}H_{33}N_3O_7$; dihydrochloride . $H_2O$ . 0.5 2-propanol: melting point 123° C. (2-propanol), $[\alpha]_D^{20}+54.5$.

EXAMPLE 12

2-O-[3-(4-Isopropyl-piperazinyl)-2-hydroxypropyl]-isosorbide-5-nitrate $C_{16}H_{29}N_3O_7$; dihydrochloride . 0.25 $H_2O$: melting point 191°–193° C. (ethanol), $[\alpha]_D^{20}+70.0$.

EXAMPLE 13

2-O-[3(4-Phenyl-piperazinyl)-2-hydroxypropyl]-isosorbide-5-nitrate $C_{19}H_{27}N_3O_7$; dihydrochloride: melting point 178° C. (decomposition) (ethanol), $[\alpha]_D^{20}+63.0$

EXAMPLE 14

2-O-<3-[4-(2-Hydroxyphenyl)-piperazinyl]-2-hydroxypropyl>-isosorbide-5-nitrate $C_{19}H_{27}N_3O_8$; dihydrochloride: melting point 188° C. (decomposition) (ethanol), $[\alpha]_D^{20}+57.5$

EXAMPLE 15

2-O-<3-[4-(2-Chlorophenyl)-piperazinyl]-2-hydroxypropyl>-isosorbide-5-nitrate $C_{19}H_{26}ClN_3O_7$; dihydrochloride: melting point 135° C. (ethanol/ether), $[\alpha]_D^{20}+61.0$.

EXAMPLE 16

2-O-<3-[4-(2-Fluorophenyl)-piperazinyl]-2-hydroxypropyl>-isosorbide-5-nitrate $C_{19}H_{26}FN_3O_7$; dihydrochloride: melting point 143°–145° C. (decomposition) (ethanol), $[\alpha]_D^{20}+61.5$.

EXAMPLE 17

2-O-<3-[4-(2-Methoxyphenyl)-piperazinyl]-2-hydroxypropyl>-isosorbide-5-nitrate $C_{20}H_{29}N_3O_8$; dihydrochloride: melting point 176°–177° C. (decomposition) (ethanol), $[\alpha]_D^{20}+60.0$.
High-melting diastereoisomer: dihydrochloride: melting point 178°–182° C. (decomposition) (ethanol), $[\alpha]_D^{20}+74.0$. Low-melting diastereoisomer: dihydrochloride: melting point 162°–165° C. (decomposition) (ethanol), $[\alpha]_D^{20}+50.0$.

EXAMPLE 18

5-O-<3-[4-(2-Methoxyphenyl)-piperazinyl]-2-hydroxypropyl>-isosorbide-2-nitrate $C_{20}H_{29}N_3O_8$; dihydrochloride: melting point 174° C. (decomposition) (ethanol), $[\alpha]_D^{20}+32.5$.

EXAMPLE 19

5-O-<3-[4-(2-Methoxyphenyl)-piperazinyl]-2-hydroxypropyl>-isomannide-2-nitrate $C_{20}H_{29}N_3O_8$; dihydrochloride: melting point 163°–164° C. (decomposition) (ethanol), $[\alpha]_D^{20}+129.0$.

EXAMPLE 20

5-O-<3-[4-(2-Methoxyphenyl)-piperazinyl]-2-hydroxypropyl>-isoidide-2-nitrate $C_{20}H_{29}N_3O_8$; dihydrochloride: melting point 185° C. (ethanol) $[\alpha]_D^{20}+26.5$.

EXAMPLE 21

2-O-<3-[4-(3-Methoxyphenyl)-piperazinyl]-2-hydroxypropyl>-isosorbide-5-nitrate $C_{20}H_{29}N_3O_8$; dihydrochloride: melting point 171° C. (decomposition) (ethanol), $[\alpha]_D^{20}+60.0$.

EXAMPLE 22

2-O-<3-[4-(4-Methoxyphenyl)-piperazinyl]-2-hydroxypropyl>-isosorbide-5-nitrate $C_{20}H_{29}N_3O_8$; dihydrochloride: melting point 185° C. (decomposition) (ethanol), $[\alpha]_D^{20}+60.0$.

EXAMPLE 23

2-O-<3-[4-(2-Ethoxyphenyl)-piperazinyl]-2-hydroxypropyl>-isosorbide-5-nitrate $C_{21}H_{31}N_3O_8$; dihydrochloride.0.5 $H_2O$: melting point 173° C. (ethanol), $[\alpha]_D^{20}+59.0$.

EXAMPLE 24

2-O-<3-[4-(2,4-Dimethoxyphenyl)-piperazinyl]-2-hydroxypropyl>-isosorbide-5-nitrate $C_{21}H_{31}N_3O_9$; dihydrochloride: melting point 185° C. (decomposition) (ethanol), $[\alpha]_D^{20}+58.0$.

EXAMPLE 25

2-O-<3-[4-(2-Methylphenyl)-piperazinyl]-2-hydroxypropyl>-isosorbide-5-nitrate $C_{20}H_{29}N_3O_7$; oxalate.0.5 $H_2O$: melting point 68°–71° C. (2-propanol), $[\alpha]_D^{20}+59.5$.

EXAMPLE 26

2-O-<3-[4-(2-Ethylphenyl)-piperazinyl]-2-hydroxypropyl>-isosorbide-5-nitrate $C_{21}H_{31}N_3O_7$; dihydrochloride: melting point 155°–156° C. (ethanol) $[\alpha]_D^{20}+62.0$.

EXAMPLE 27

2-O-<3-[4-(2,6-Dimethylphenyl)-piperazinyl]-2-hydroxypropyl>-isosorbide-5-nitrate $C_{21}H_{31}N_3O_7$; dihydrochloride: melting point 135°–137° C. (decomposition) (ethanol), $[\alpha]_D^{20}+67.0$.

EXAMPLE 28

2-O-<3-[4-(2-Nitrophenyl)-piperazinyl]-2-hydroxypropyl>-isosorbide-5-nitrate $C_{19}H_{26}N_4O_9$; hydrochloride: melting point 133° C. (ethanol)G, $[\alpha]_D^{20}+60.5$.

EXAMPLE 29

2-O-<3-[4-(3-Trifluoromethylphenyl)-piperazinyl]-2-hydroxypropyl>-isosorbide-5-nitrate $C_{20}H_{26}N_3O_7$; dihydrochloride: melting point 153°–156° C. (decomposition) (ethanol), $[\alpha]_D^{20}+56.0$.

EXAMPLE 30

2-O-<3-[4-(3,4-Methylenedioxyphenyl)-piperazinyl]-2-hydroxypropyl>-isosorbide-5-nitrate $C_{20}H_{27}N_3O_9$; dihydrochloride: melting point 179°–180° C. (decomposition) (ethanol), $[\alpha]_D^{20}+56.0$.

EXAMPLE 31

2-O-<3-[4-(2-Pyridyl)-piperazinyl]-2-hydroxypropyl>-isosorbide-5-nitrate $C_{18}H_{26}N_4O_7$; melting point 95°–97° C. (methanol), $[\alpha]_D^{20}+79.0$; dihydrochloride . 0.25 $H_2O$ . 0.5 2-propanol: melting point 84°–87° C. (2-propanol), $[\alpha]_D^{20}+56.5$

EXAMPLE 32

2-O-[3-(4-Pyrimidin-2-yl-piperazinyl]-2-hydroxypropyl]-isosorbide-5-nitrate $C_{17}H_{25}N_5O_7$; dihydrochloride . 2 $H_2O$: melting point 104°–105° C. (ethanol), $[\alpha]_D^{20}+51.5$

EXAMPLE 33

2-O-[3-(2-Benzoyl[1,4]dioxinyl-methylamino)-2-hydroxypropyl]-isosorbide-5-nitrate $C_{18}H_{24}N_2O_9$; hydrochloride: melting point 135°–138° C. (2-propanol/ether), $[\alpha]_D^{20}+71.0$.

EXAMPLE 34

2-O-<3-[2-(2-Methoxyphenoxy)-ethylamino]-2-hydroxypropyl>-isosorbide-5-nitrate $C_{18}H_{26}N_2O_9$; oxalate . 0.25 $H_2O$: melting point 135°–138° C. (ethanol) $[\alpha]_D^{20}+64.0$.

EXAMPLE 35

2-O-<3-[2-(3-Methoxyphenoxy)-ethylamino]-2-hydroxypropyl>-isosorbide-5-nitrate $C_{18}H_{26}N_2O_9$; oxalate . 0.25 $H_2O$; melting point 161°–163° C. (ethanol), $[\alpha]_D^{20}+65.0$.

EXAMPLE 36

2-O-<3-[4-(4-Methoxyphenoxy)-ethylamino]-2-hydroxypropyl>-isosorbide-5-nitrate $C_{18}H_{26}N_2O_9$; hydrochloride: melting point 111°–113° C. (2-propanol), $[\alpha]_D^{20}+70.0$.

EXAMPLE 37

2-O-<3-[2-(2-Hydroxyphenoxy)-ethylamino]-2-hydroxypropyl>-isosorbide-5-nitrate $C_{17}H_{24}N_2O_9$; hydrochloride: m.p. 173°–176° C. (ethanol), $[\alpha]_D^{20}+69.0$.

High melting diasteroisomer: hydrochloride: m.p. 185°–187° C. (decomposition) (methanol), $[\alpha]_D^{20}+65.0$.

Low melting diastereomer: hydrochloride: m.p. 141°–146° C. (ethanol), $[\alpha]_D^{20}+79.5$.

EXAMPLE 38

2-O-<3-[2-(3-Hydroxyphenoxy)-ethylamino]-2-hydroxypropyl>-isosorbide-5-nitrate $C_{17}H_{24}N_2O_9$; semioxalate . $H_2O$: m.p. 72° C. (2-propanol), $[\alpha]_D^{20}+61.5$.

EXAMPLE 39

2-O-<3-[2-(4-Hydroxyphenoxy)-ethylamino]-2-hydroxypropyl>-isosorbide-5-nitrate $C_{17}H_{24}N_2O_9$; oxalate . 0.52-propanol . 0.25 $H_2O$: m.p. 51° C. (2-propanol) $[\alpha]_D^{20}+59.5$.

EXAMPLE 40

The following is given as an example of one of the new intermediate products VIII:

5-O-<3-[4-(2-Methoxyphenyl)-piperazinyl]-2-hydroxypropyl>-isosorbide $C_{20}H_{30}N_2O_6$; oxalate: m.p. 69°–70° C. (precipitated in diethyl ether with the stoichiometric amount of oxalic acid), $[\alpha]_D^{20}+30.5$.

We claim:

1. A compound of the formula I

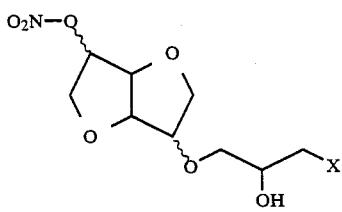
(I)

in which X is a benzo[1,4]dioxinyl-2-methylamine radical of the formula

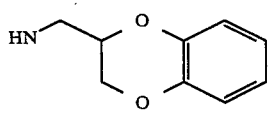

a phenoxyethylamino radical of the formula

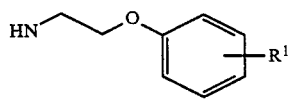

in which $R^1$ is hydrogen, hydroxyl or a $C_1$–$C_3$-alkoxy radical, and the substituent $R^1$ can be in the o-, m- or p-position, or X is one of the following radicals:

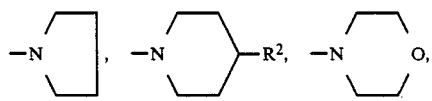

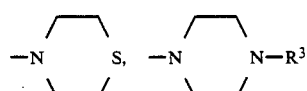

in which $R^2$ represents hydrogen or an unsubstituted or mono-, di- or tri- substituted phenyl radical, wherein the substituents on the phenyl can be the same or different and are selected from $C_1$–$C_3$ alkyl, $C_1$–$C_3$ alkoxy, halogen, nitro and trifluoromethyl, and in which $R^3$ represents straight chain or branched $C_1$–$C_6$ alkyl, hydrogen,

wherein $R^6$ is $C_1$–$C_7$ alkyl, phenyl, phenyl substituted with $C_1$–$C_4$ alkyl, or

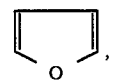

benzyl, benzhydryl, pyridyl, pyrimidinyl, or unsubstituted or substituted phenyl of the formula

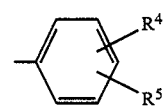

in which $R^4$ and $R^5$ can be identical or different and each represents hydrogen, hydroxyl, $C_1$–$C_6$ alkyl $C_1$–$C_6$ alkoxy, halogen, nitro or trifluoromethyl, or in which $R^4$ and $R^5$ together form a methylenedioxy group, and pharmaceutically acceptable salts thereof.

2. A compound according to claim 1, which is a compound of the formula Ia

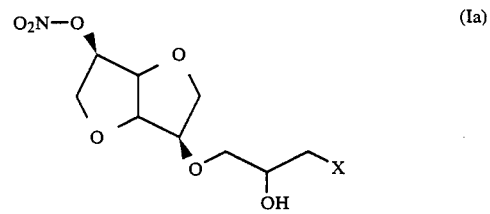
(Ia)

in which the two substituents in the 2- and 5-position are in the endo-position and X is as defined in claim 1 or a salt thereof.

3. A compound according to claim 1 which is a compound of the formula Ib

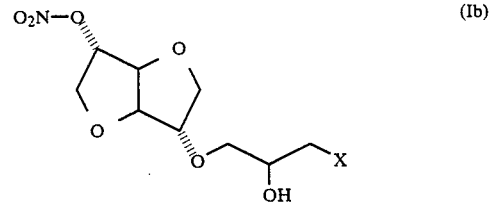
(Ib)

in which the two substituents in the 2- and 5-position are in the exo-position and X is as defined in claim 1 or a salt thereof.

4. An aminopropanol derivative as claimed in claim 1 which is a compound of the formula Ic or Id

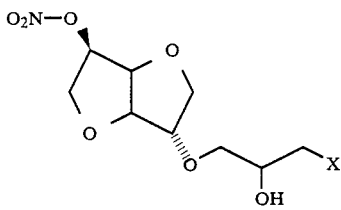

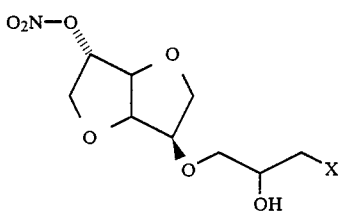

in which the substituent in the 2-position each time occupies the exo-position and the substituent in the 5-position each time occupies the endo-position and X is as defined in claim 1 or a salt thereof.

5. A compound according to claim 1 which is a separate diastereomer of uniform configuration or a salt thereof.

6. A compound according to claim 2 which is a separate diastereomer of uniform configuration or a salt thereof.

7. A compound according to claim 3 which is a separate diastereomer of uniform configuration or a salt thereof.

8. A compound according to claim 4 which is a separate diastereomer of uniform configuration or a salt thereof.

9. A pharmaceutical composition for treating a condition selected from the group consisting of angina pectoris, systemic hypertension, and pulmonary hypertension comprising an amount of a compound according to claim 1 effective against one of the foregoing conditions and a pharmaceutically acceptable carrier.

10. A composition according to claim 9, wherein said compound is a compound of the formula Ia

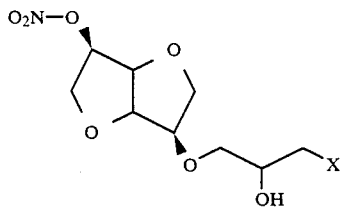

in which the two substituents in the 2- and 5-position are in the endo-position and X is as defined in claim 9 or a salt thereof.

11. A composition according to claim 9 wherein said compound is a compound or the formula Ib

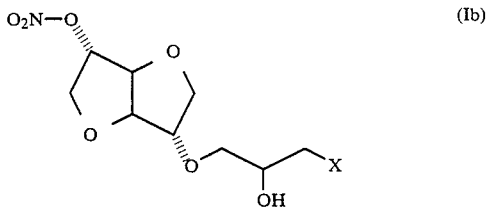

in which the two substituents in the 2- and 5-position are in the exo-position and X is as defined in claim 9 or a salt thereof.

12. A composition according to claim 9 wherein said compound is a compound of the formula Ic or Id

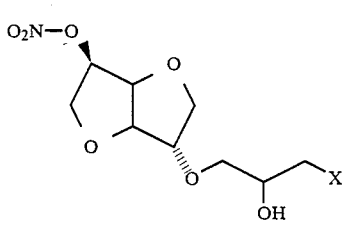

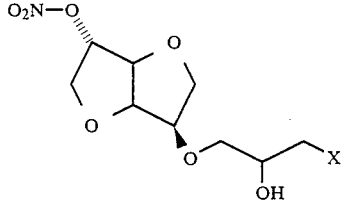

in which the substituent in the 2-position each time occupies the exo-position and the substituent in the 5-position each time occupies the endo-position and X is as defined in claim 9 or a salt thereof.

13. A composition according to claim 9 wherein said compound is a separate diastereomer of uniform configuration or a salt thereof.

14. A composition according to claim 10 wherein said compound is a separate diastereomer of uniform configuration or a salt thereof.

15. A composition according to claim 11 wherein said compound is a separate diastereomer of uniform configuration or a salt thereof.

16. A composition according to claim 12 wherein said compound is a separate diastereomer of uniform configuration or a salt thereof.

17. A method of treating a condition selected from the group consisting of angina pectoris, systemic hypertension, and pulmonary hypertension comprising administering to a mammal in need of such treatment an amount of a compound according to claim 1 effective against one of the foregoing conditions.

18. A method according to claim 17, wherein said compound is a compound of the formula Ia

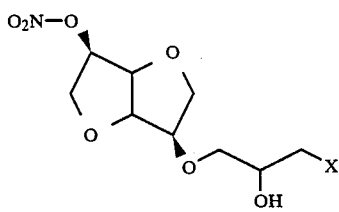 (Ia)

in which the two substituents in the 2- and 5-position are in the endo-position and X is as defined in claim 17 or a salt thereof.

19. A method according to claim 17 wherein said compound is a compound or the formula Ib

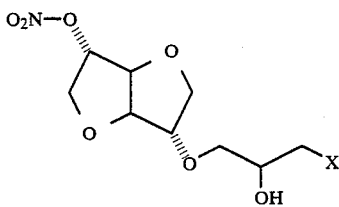 (Ib)

in which the two substituents in the 2- and 5-position are in the exo-position and X is as defined in claim 17 or a salt thereof.

20. A method according to claim 17, wherein said compound is a compound of the formula Ic or Id

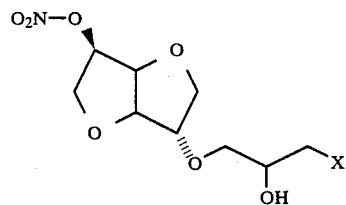 Ic

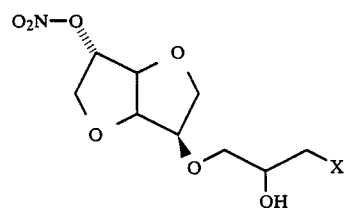 Id in which the substituent in the 2-position each time occupies the exo-position and the substituent in the 5-position each time occupies the endo-position and X is as defined in claim 17 or a salt thereof.

21. A method according to claim 17 wherein said compound is a separate diastereomer of uniform configuration or a salt thereof.

* * * * *